United States Patent [19]
Slavin

[11] Patent Number: 4,624,263
[45] Date of Patent: * Nov. 25, 1986

[54] PORTABLE ELECTROCARDIOGRAPH WITH DIGITALLY-PRINTING WAVEFORM DISPLAY

[75] Inventor: Martin J. Slavin, Dix Hills, N.Y.

[73] Assignee: Advanced Medical Electronics Developments Limited Partnership, White Plains, N.Y.

[*] Notice: The portion of the term of this patent subsequent to Nov. 20, 2001 has been disclaimed.

[21] Appl. No.: 643,620

[22] Filed: Aug. 24, 1984

Related U.S. Application Data

[63] Continuation-in-part of Ser. No. 526,260, Aug. 25, 1983, Pat. No. 4,483,346.

[51] Int. Cl.$^4$ .............................................. A61B 5/04
[52] U.S. Cl. .................................................... 128/710
[58] Field of Search ............... 128/696, 710, 711, 712; 346/33 ME; 364/415, 417

[56] References Cited

U.S. PATENT DOCUMENTS

| | | | |
|---|---|---|---|
| 3,369,249 | 2/1968 | Argy et al. | 128/710 |
| 3,934,267 | 1/1976 | Kosaka et al. | 128/711 |
| 4,483,346 | 11/1984 | Slavin | 128/710 |

FOREIGN PATENT DOCUMENTS

| | | | |
|---|---|---|---|
| 246619 | 12/1960 | Australia | 128/710 |
| 502072 | 3/1939 | United Kingdom | 128/710 |

Primary Examiner—William E. Kamm
Attorney, Agent, or Firm—Blum, Kaplan, Friedman, Silberman & Beran

[57] ABSTRACT

An electrocardiograph for connection to sensors outputting analog electrical signals and having at least one sensor outputting electrical signals is provided. At least one of the analog signals is sampled, converted from analog to digital form and stored in a memory means. A processor writes consecutively sampled digitalized signals represented by a predetermined duration of the analog sensor output signal to addresses of the memory for storage in consecutive order. The processor applies the stored data from the addresses in consecutive order through a printer which prints a series of portions of a curve representative of the analog signal to produce a cardiogram extending in the direction of advance of the print medium. A magnetic tape cassette is provided for storage of data and an audible alarm means is also provided. The memory may also store programs for analysing the data.

41 Claims, 5 Drawing Figures

PORTABLE ELECTROCARDIOGRAPH WITH DIGITALLY-PRINTING WAVEFORM DISPLAY

CROSS-REFERENCE TO RELATED APPLICATION

This is a continuation-in-part of application Ser. No. 526,260 filed Aug. 25, 1983, now U.S. Pat. No. 4,483,346.

BACKGROUND OF THE INVENTION

This invention relates generally to a cardiograph of the type used to provide a record of data from conventional electrocardiograph sensors which are applied to a patient's body and more particularly to a small, hand held, battery powered miniature phono- and electrocardiograph which may be conveniently carried by doctors, nurses, interns, technicians and emergency service personnel. Conventional ECG machines are used under controlled conditions wherein the patient is carefully prepared for the measurements which are to be made. The machines are generally bulky and expensive and for both reasons are not considered portable such that a doctor would transport them in his normal rounds, nor would these instruments be practical for transport by nurses, technicians and the like. Thus the use of ECG machines has been limited although the permanent record which these machines provide of a patient's condition at a given moment of time is an invaluable tool to the practioner.

Another disadvantage of conventional machines outputting a cardiogram is the size and delicateness of the printer which is required to produce a substantially instantaneous analog representation of the ECG signals as they are detected. The ability of the recording pen to accurately follow the inputted electrical driving signals leaves room for improvement and the use of an oscilloscope, while accurately following the electrical signals, provides no permanent record unless supplementary equipment for photographic recording is provided. Thus the complexity of such devices is compounded and portability enabling on-site utility is further limited.

Further, it would be medically useful to provide a permanent record of a signal representative of the audible output of a stethoscope, so as to provide a permanent record, and to permit comparison with an electrocardiogram of the patient.

My prior application provided a miniature phono- and electrocardiograph which is small, lightweight and therefore portable, and provides an accurate, permanent record of ECG and phono inputs as from a stethoscope.

What is additionally needed is the provision of additional features in a miniature phono- and electrocardiograph, including micro-cassette data storage, audible alarm, synthesized speech annunciating, phono- and electrocardiograph data processing including storage, printing and/or display of results, and processing of signals from auxillary devices including storage, printing and/or display.

SUMMARY OF THE INVENTION

Generally speaking, in accordance with the invention, a miniature phono- and electrocardiograph is provided especially suitable for hand held portable operation. The miniature phono- and electrocardiograph is hand held and battery powered. The device includes a digitally driven miniature printer capable of simultaneously printing data received from at least two body sensors. Signals from conventional ECG electrodes or from a phono output of a stethoscope (PCG) such as the differential stethoscope as disclosed in my U.S. Pat. No. 4,438,772, are selected by multiplexing in accordance with machine instructions provided by the user. The selected multiplex signals are converted from analog to digital format and stored in a random access memory all under control of a microprocessor. Substantially concurrently with the input of data to the random access memory, said data may be read out under control of the microprocessor and input to the digitally driven printer to provide a printed record of the original ECG and PCG inputs. The speed of reading data from the memory to drive the printer is slower than the speed of writing data into memory from the sensors.

Outputs are provided on the device for interfacing with an oscilloscope and with a modem for transmission of the digitized data by telephone or other data transmission means for analysis at a remote location. A keyboard allows the user to select for printout among the various ECG electrodes and the phono input from the stethoscope which may be simultaneously connected to the miniature phono- and electrocardiograph. The user also inputs identification data by means of the keyboard, for example, the patient's name, the operator's name, date, time, and the like and identification of the selected channels which are being recorded. The printer prints this information on the record with the printout of the actual ECG and PCG data. Date and time information can be automatically printed from an interval timer in the device. The keyboard may also permit selection of the gain, time base, number of beats to be recorded, special filters and other output signal-defining features, by applying control signals to the microprocessor. A display such as a liquid crystal display, indicates the identification data as it is input by the user to permit checking for accuracy, and also displays instructions for the user and requests for information from the user as required for a complete record, under control of the microprocessor and using data stored in a read only memory. A rechargable battery powers all circuits.

The display may include a dot-matrix sufficient to provide a visual display of at least one selected ECG or PCG curve. A microcassette device may be provided for the storing of ECG and PCG data, the microprocessor permitting selective printing of the stored data, display of the stored data on the display or transmission of the stored data to an exterior device, as directed by the operation of the keyboard. Alarm means may also be provided under the control of the microprocessor to produce an alarm indication of cessation of natural R-wave, or heart rate above or below selected values. A voice synthesizer may be provided for oral alarms or oral instructions to the user.

Selected data processing programs can be stored in memory, permitting analysis of the ECG and PCG data and recordation by the printer or display of the results. Such programs can include fast fourier transform of the data, spectral-analysis and diagnostic analysis. Representative abnormal ECG data can also be stored in memory, permitting selected printout in side-by-side relation of typical abnormal data and the patient's ECG data for aid in diagnosis.

Accordingly, it is an object of this invention to provide an improved miniature phono- and electrocardiograph which is small and can be hand held.

Another object of this invention is to provide an improved miniature phono- and electrocardiograph which is battery powered and can be used in the field under uncontrolled conditions.

A further object of this invention is to provide an improved miniature phono- and electrocardiograph which can select for printing among a plurality of ECG inputs and a phono input (PCG) from a stethoscope.

A still further object of the invention is to provide a portable electrocardiograph incorporating a digitally controlled printer which prints at a rate slower than the rate of input of the ECG signals into the device.

Still another object of this invention is to provide an improved miniature phono- and electrocardiograph which provides a permanent, accurate printed record of the recorded data, including identifying information.

Yet another object of this invention is to provide an improved miniature phono- and electrocardiograph which provides ongoing instructions and requests information from the user as required for a complete and accurate recording of data.

A still further object of this invention is to provide an improved miniature phono- and electrocardiograph incorporating a micro-cassette data storage capability and/or a visual data display capability.

Still another object of this invention is to provide an improved miniature phono- and electrocardiagraph which includes the capability of performing analysis of ECG data, PCG data and/or data from auxilliary devices and having the further capability of storing, printing and/or displaying the results.

A still further object of the invention is to provide a portable phono- and electrocardiagraph which provides audible alarm functions and may provide voice synthesized alarm and instructions.

A still further object of this invention is to provide an improved miniature phono- and electrocardiograph incorporating a micro-cassette data storage capability and/or a visual data display capability.

Still other objects of this invention will in part be obvious and will in part be apparent from the specification.

The invention accordingly comprises the features of construction, combinations of elements, and arrangements of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

With reference to the Figures, the phono- and electrocardiograph 10 in accordance with the invention includes a case consisting of an upper member 12a and a lower member 12b joined by hinges 12d and latch members 12c. The case has on the left side surface thereof a plurality (in this embodiment, twelve) of input jacks 14 for connection with ECG electrodes which may be applied in the conventional manner to a patient for the purpose of producing cardiograms. A jack 20 on the right side of the case provides for input of the electrical (phono) output (PCG) of a stethoscope having an electro-acoustic transducer such as the differential stethoscope of the type disclosed in my U.S. Pat. No. 4,438,772. This input provides an analog signal representative of the patient's heartbeat and heart sounds. Jack 20 may also provide an input for other auxiliary devices as more particularly described below.

The phono- and electrocardiograph 10 also includes a keyboard 22 on the top surface thereof for inputting alpha-numeric information as explained more fully hereinafter, and a liquid crystal dot matrix display 24 on the top surface thereof for providing a visual indication of the inputs to the keyboard 22 and other information. A printer 26 mounted within the case prints on a recording sheet 28 which is supplied to the printer 26 from a roll 30 retained within the case 12 and made visible by a transparent window 32.

The phono- and electrocardiograph 10 includes battery pack 34 which is chargeable by means of a input jack 36 located on the right side surface of the case opposite from the ECG input jacks 14. An ON-OFF switch 38, which controls application of battery power to the other electrical elements of the phono- and electrocardiograph 10 is also located on the right side surface of the case 12. A first output jack 40 provides an analog output of any selected signal which is being input at the jacks 14, 20 for the purpose of applying the signal to another cardiograph device, or to an oscilloscope for display. A second output jack 42 can selectively provide digitized, multiplexed data output signals representative of one or more of the inputs to jacks 14, 20 in a format suitable for data transmission. The phono- and electrocardiograph 10 may include a modem 43 coupled to output jack 42 for transmitting the data by telephone or for transmitting the recorded data to temporary or permanent storage externally of the phono- and electrocardiograph 10 of this invention.

A micro-cassette magnetic tape deck 66 is mounted in the lower member 12b of the case with access provided by door 68. A speaker 80 is mounted on upper member 12a of the case.

Figure 4:
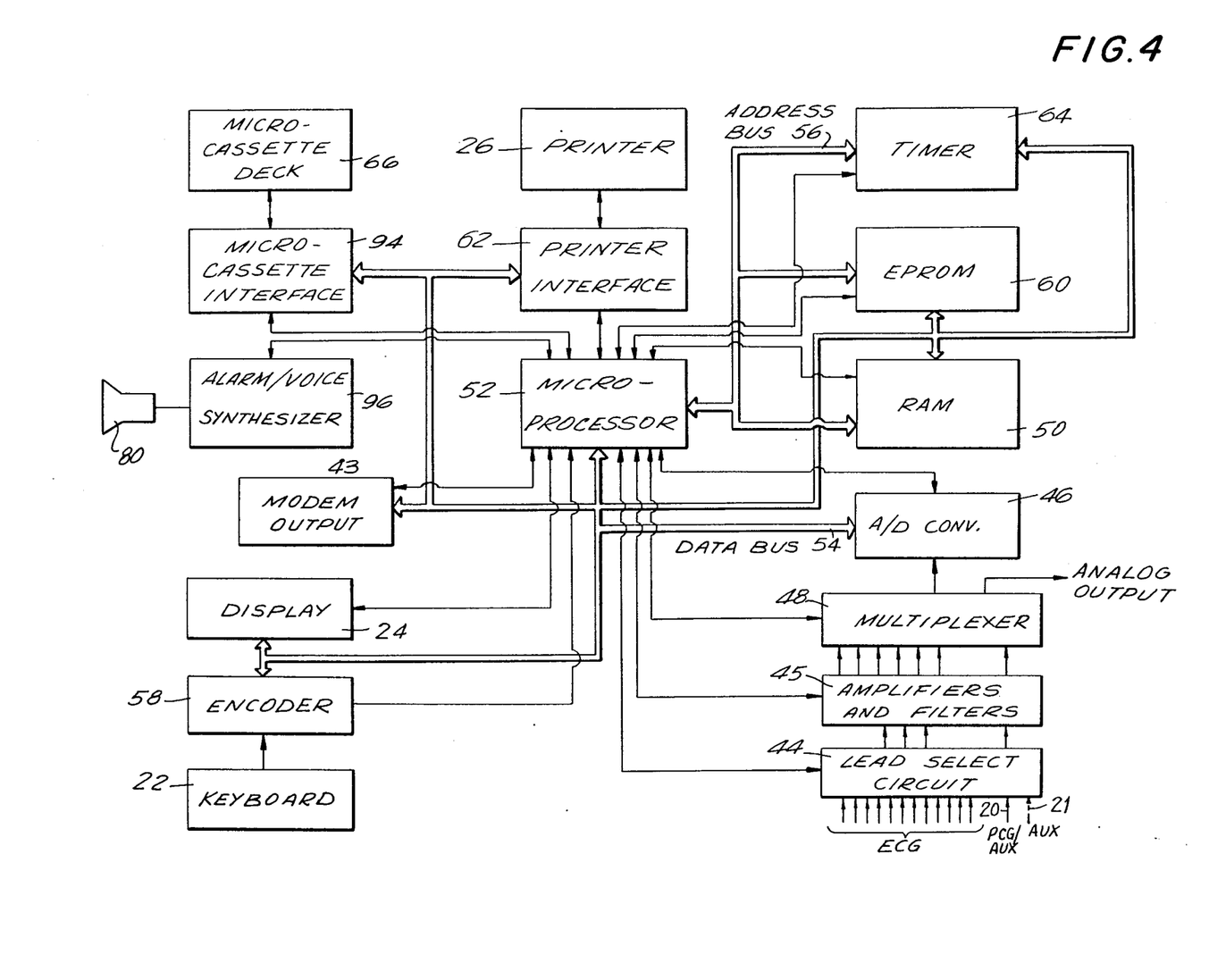
FIG. 4 is a functional block diagram of a miniature phono- and electrocardiograph in accordance with the invention.

In the embodiment depicted, twelve ECG inputs are provided, one, for example the right leg input, serving as a reference signal in a conventional manner. Additional ECG inputs can be provided if desired. As best seen in FIG. 4, the ECG or phono signals (PCG) received at the jacks 14, 20 are input to lead select circuit 44 where desired input ECG signals or combinations thereof are selected under the direction of a microprocessor 52. The analog inputs are then fed to an analog to digital converter 46 by way of amplifiers and filters 45 and a multiplexer 48. Multiplexer 48 operates under the direction of a microprocessor 52, which in turn is controlled by instructions from the user inputted through keyboard 22 or by instructions stored in a read only memory (EPROM 60) as more particularly described below.

Figure 1:
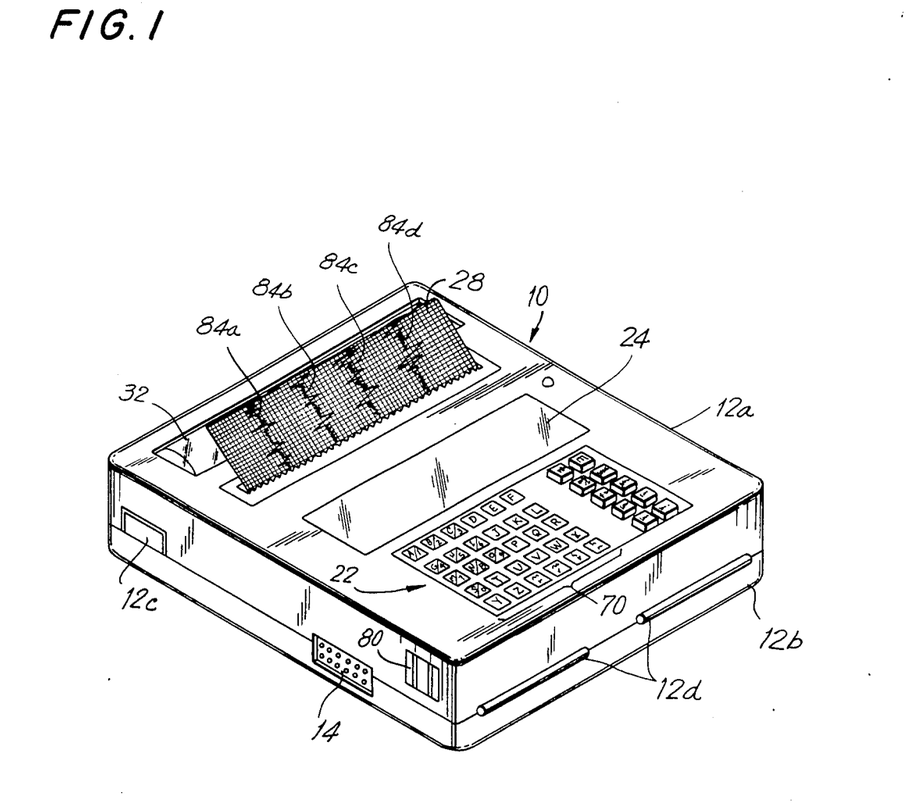
FIG. 1 is a top, left, front perspective view of a miniature phono- and electrocardiograph in accordance with the invention.
Figure 2:
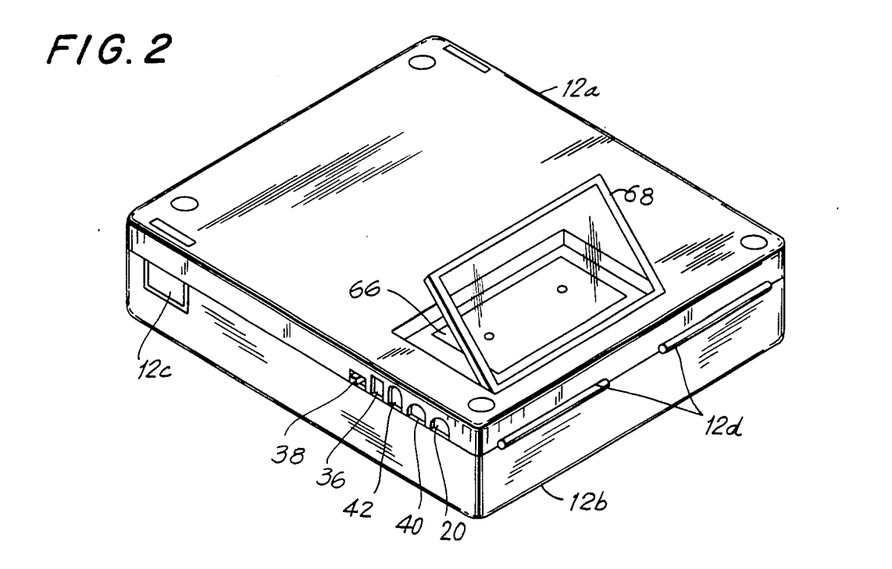
FIG. 2 is a bottom, right, front perspective view of the phono- electrocardiagraph of FIG. 1.

Lead select circuit 44 includes microprocessor controlled switches which selectively direct the input signals from jacks 14, 20 to addition, subtraction, averaging and filter circuits to produce the desired combination of inputs which are more conventionally used in electrocardiographs, as well as such picture combinations as may be desired. Thus, by way of example, among the combinations of signals frequently produced are the difference between the left arm (LA) and right arm (RA) inputs (denominated I), and the difference between the right arm input (RA) and the average of the left arm (LA) and left leg (LL) inputs (denominated AVR). As more particularly shown in FIG. 5, the individual or combined inputs can be selectively passed through one or more amplifiers and filters. The amplification serves to condition the signals to provide maximum peaks at full scale in the data storage and printing process. The three ECG signals from jacks 14 are particularly small and must be amplified by instrument amplifiers 82a, 82b and 82c, respectively. Three such amplifiers are shown in this embodiment so that three channels of ECG data can be simultaneously printed on paper 28 as shown by curves 84a, 84b and 84c (FIG. 1). The instrument amplifiers are characterized by high common mode rejection. An additional variable amplifier stage 86a, 86b and 86c, respectively, is provided in each channel. The variable filters permit gain selection in each channel under the control of the microprocessor. A first filter 88a, 88b and 88c, respectively, is provided in each channel to further condition the signal by eliminating noise. These filters may break at about 100 Hz.

Figure 5:
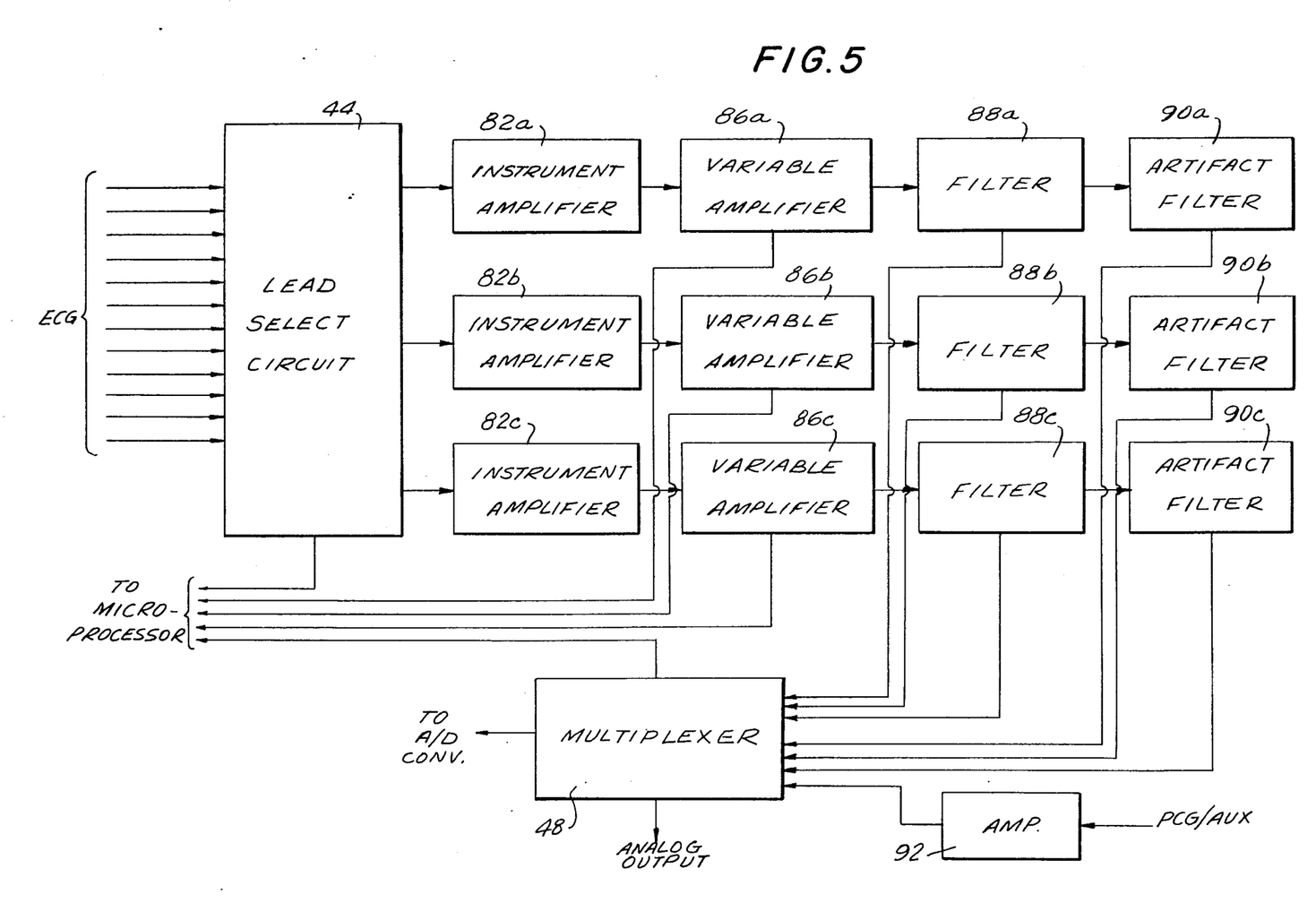
FIG. 5 is a block diagram of the input section of the phono- and electrocardiograph of FIG. 4.

Artifact filters 90a, 9b and 90c, respectively, are provided in each channel. The artifact filter may be down about 18b at about 60 Hz, breaking at about 20 Hz. The artifact filters filter the effect of various electrical signals. One or more of the individual or combined inputs, after filtering if desired, is selected by the multiplier 48 as directed by the multiprocessor for sampling, and is then digitized by A/D converter 46.

Thus, the user through the keyboard and microprocessor, can select whether the signal to be digitized is filtered or unfiltered by the artifact filter associated therewith. An audio amplifier 92 is used to apply the PCG/AUX signal. The sampled digitized data of the selected inputs or combinations of inputs are stored in consecutive addresses of a random access memory 50 (RAM). If four signals are to be printed, displayed or transmitted, each memory address or consecutive memory addresses contain essentially contemporaneous samples of the four signals selected for printing, display or transmission. Since the sampling rate is selected to be very high as compared to the rate of the sampled signals, the sampled signal portions stored in RAM 50 provide an accurate representation of the desired signal, and where there are four such signals, they can be deemed to be contemporaneous. In one embodiment a sampling rate of about 2,000 per second is used.

Microprocessor 52 controls operation of the multiplexer 48, analog to digital converter 46, and RAM 50, including the selection of addresses in the RAM 50 for storage of the digitized data. The data from the analog to digital converter 46 is transmitted to the microprocessor 52 by way of a two way data bus 54 which also provides data input to the RAM 50. An address bus 56, connects the microprocessor 52 to the RAM 50 allowing the microprocessor 52 to control address selection for storage of digitized signal data.

The microprocessor is adapted to process the sampled and digitized input data as instructed by the user by means of keyboard 22. Microprocessor 43 can be instructed by the user through keyboard 22 to adjust the gain of the input signals, to set the number of beats of the input signal to be recorded and to set the time base of the portion of the input signal to be recorded. Due to practical limitations in the size of RAM 50, only a limited number of beats of ECG signal or phono signal can be processed at each operation of the device. However, with provision of additional memory, additional beats can be stored. Time base may be adjusted by selecting the speed of feed of print medium 28. Gain can be expressed in terms of sensitivity, the number of millimeters of deflection on the print out per millivolts of input. Both time base and gain can be controlled continuously through the keyboard but in one embodiment, three preset choices for each are provided, selected by its user through the keyboard, and remaining unchanged from use to use until changed.

Numbers, letters or instructions input by depressing keys on the keyboard 22 are encoded in an encoder 58 into signals suitable for transmission on common data bus 54. These encoded signals are translated into signals for driving the liquid crystal display or the printer by the microprocessor, using codes stored in the electrically programmable read only memory (EPROM) 60 in a conventional manner. Using the keys on the keyboard, the user may insert data identifying the equipment operator, the patient and channels or signals which are selected for printing. The phono- and electrocardiograph is user-friendly in that EPROM 60 includes instructions for the user, directing the user in the proper sequence of operations and requesting particular inputs from the user at the proper time such that these inputs may be stored in RAM 50 in the proper addresses selected by the microprocessor 52. The instructions from EPROM 60 to the user are in the form of instruction signals driving the display 24, alerting the user to his next operation or identification data input. The displayed instructions can be alphanumeric. The microprocessor also displays the inputs inserted by the user to insure accuracy of inputs. The display can be of any form but is preferably by a liquid crystal display. If a dot matrix display is used, the sampled, digitized data could be displayed on display 24. As directed by the keyboard, the data displayed on display 24 can be from RAM 50 or directly from A/D converter 48.

The printer 26 is of any conventional digitally driven type which provides a print head traversing on a carriage across the face of the print medium 28 or the traverse of the print medium laterally on a carriage relative to a print head and providing for feeding of the print medium 28 in a direction transverse to the motion of the carriage.

The signal data stored in the RAM 50 is input to the printer 26 from consecutive addresses in the order of storage, starting essentially simultaneously with data input. The data from the RAM 50 is read by the microprocessor and input to a printer interface 62 which drives the print head to print on the recording medium 28. Printing is effected when the carriage reaches the lateral position in its traverse across the medium corresponding to the digitized data stored in the memory address which has been read. The memory address is advanced in correlation with the motion of the print head across the print media, coordinated by the microprocessor 52 when data for each curve is stored in separate memory addresses. In an embodiment where each address contains data for four curves, the memory address is advanced after each carriage traverse and advancement of the print medium 28 relative to the print head. In both embodiments the print medium 28 is advanced upon completion of printing in each carriage traverse.

In one embodiment, the printer is a printer having an ink pen which is displaced toward and away from the paper by a solenoid and laterally of the paper on a carriage. An incremental length of each of the curves is produced on each traverse of the carriage. The paper may be advanced or withdrawn during each traverse, the pen being engaged with the print medium or withdrawn as required to produce the desired curve sections.

Figure 3:
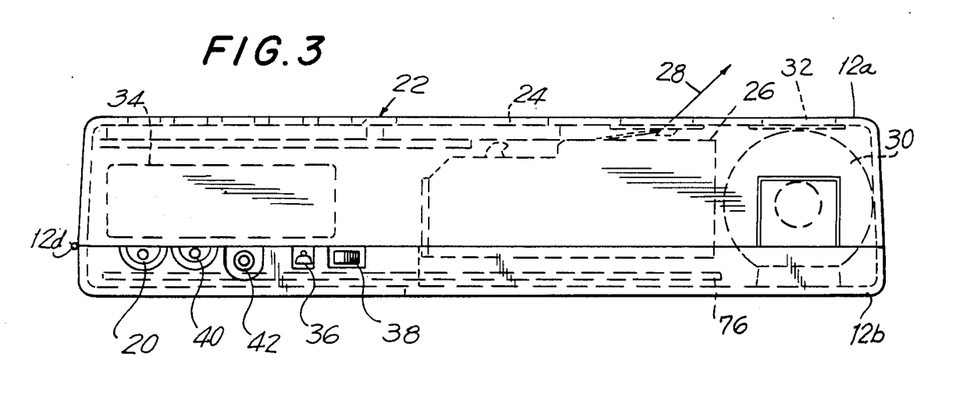
FIG. 3 is a right side view of the electrocardiograph of FIG. 1.

A timer circuit 64 also provides actual time and date information which may become a portion of the data stored in the RAM 50 for each operation of the device for later printing or such time and date information may be read from the timer circuit and directly transmitted to the printer for printing out on the recording medium 28 when the recorded data signals are printed. Timer 64 may be set by operation of the keyboard under the control of the microprocessor. Address bus 56 is also connected to EPROM 60 and timer 64 to enable the microprocessor to access these devices for reading data from them and for setting the timer. Data bus 54 and address bus 56 are preferably common to a plurality of circuit elements as shown in FIG. 3 and are operated as shared, multiplexed buses to minimize cost and size.

The printer 26 prints a segment (a dot or line) of each of the one to four (one PCG/AUX and three ECG) selected curves on the recording medium 28 in each traverse of the print head carriage in correspondence with the two data points which are stored in RAM 50. The printer may be of any digitally driven type, for example, a pen printer (where the pen is selectively engaged and lifted off the paper), wire dot printer, an ink jet printer, a thermal printer operating with sensitized paper, etc. In the case of a dot printer, if two curves are to be printed, two dots, one from each data signal, are printed in each traverse of the carriage. With a pen printer, for example, a dot or line portion is printed for each curve of the data signals in each traverse. At the beginning or end of printing of the stored data signals, the identifying data and time and date information are printed on the recording medium 28. For the identification, time and date data, the number of dots or line portions printed in each traverse depends upon the data to be printed. Whereas the data is input to the RAM memory 50 from the ECG terminals 40 and phono terminal 20 at a high sample rate and for a period of time determined by the capacity of the memory 50 and the desired duration of signal input, the rate of reading data from the RAM 50 and driving of said printer 26, is selected for optimum operation of the printer 26. Thus, the rate of data read out and printing is much lower than the data write-in rate. Therefore, printing is completed only after a time lag following completion of data input to the RAM 50, although printing begins substantially concurrently with the input of signal data to the RAM 50. The multiplexing of the addresses and data buses permits data input and printing to occur simultaneously.

Because read out of data from the RAM 50 is timed to accommodate the capabilities of the printer 26, a small, lower-speed digitally driven printer may be used in this device as compared with the analog graphing mechanisms used in the electrocardiograph devices of the prior art. Because the carriage of the printer moves at a predetermined rate across the print medium 28 regardless of the magnitude of the signal data to be recorded, a printer operating in this fashion is extremely accurate and does not experience the deficiencies of conventional electromechanical pen-type devices which respond to analog signals input thereto and suffer deficiencies resulting from the mass of the pen and its carriage. Printers which operate at lower speeds are simpler in construction and accordingly, lower in cost and high in reliability. Thus, by storing the input signal data in the memory 50 at a rapid rate sufficient to assure a large data accumulation and accuracy of the printed output, the deficiencies of the prior art are overcome, and a phono- and electrocardiograph which is sufficiently small so as to be portable and battery powered. A permanent record is provided without cumbersome set up procedures in the form of a cardiogram which is extremely accurate and permanently identified so as to avoid loss or misapplication.

It should be readily understood that the duration of sampling, that is, the amount of data which is stored temporarily for printout depends upon the size of the memory 50. The number of curves which are reproduced in one printing sequence can be varied depending upon the size of the RAM memory 50 and the degree of multiplexing which is provided. It should also be understood that a circulating memory may be used to store the data such that the content of a memory address is erased immediately after read out of that address and new data may subsequently be stored in the same memory address, thereby extending the amount of data which can be processed before the memory becomes "full".

It should also be understood that in alternative embodiments the incoming signals which had been conditioned can be printed out on the recording medium 28 with ordinate markings indicating the true scale of the signals.

As pointed out above, the display 24 can receive the data in essentially real time so that the user can observe the ECG curve and when he sees an abnormality, actuate the printer which generates a curve from data stored in the RAM 50. The storing of data in the memory can be delayed so that the observed abnormality may be printed.

Data bus 54 is also coupled to micro-cassette interface 94 which operates under the control of the microprocessor, as directed by the user through keyboard 22, to store the digitized ECG, PCG, time, machine status and/or identification data. By use of the micro-cassette, the phono- and electrocardiagraph 10 can serve as a patient monitor with long term storage. Under the control of the user through the keyboard and micro-processor, the stored data in microcassette deck 66 can be viewed on display 24, printed by printer 26 or transmitted by modem output 43.

Speaker 80 can be used to serve several purposes under the control of the micro-processor through alarm/voice synthesizer circuit 96. A tone can be sounced for each R-wave. A continuous or variable tone can be sounded if the natural R-wave ceases. A continuous tone of different loudness and/or frequency can be sounded if the heart rate rises above a predetermined level or falls below a predetermined level. Finally, by use of a conventional voice synthesizer using EPROM 60 for storage of vocabulary, verbal instructions or warnings can be given.

In operation, the operator turns the unit on by operation of the switch 38 and follows the instructions provided on the liquid crystal display 24 or given verbally, making inputs by way of the keyboard 22 and connecting the sensor leads to the proper jack terminals 14, 20. The operator makes further inputs as requested by the unit to identify himself and the patient, to select the outputs for print out, to select display or micro-cassette functions, to select alarm functions, to set the other variables such as gain, time base, number of beats, and filters, and to input the date and time unless provision has been made for the microprocessor 52 to accomplish this task automatically using data from the timer circuits 64.

In response to an instruction to begin data collection appearing on the liquid crystal display 24, and by operating the keyboard 22 in response thereto, the incoming signals are allowed to enter the signal conditioning circuits 44 for processing as described above. Substantially concurrently, the printer commences operation, printing out the selected signal inputs as curves as the print media 28 moves out of the printer 26.

In one embodiment, ten of the keys of keyboard 22 in group 70 are used for numeric inputs. Twenty-six of the keys of group 70 are used for letter inputs, some keys performing both letter and numeric functions. The remaining keys of group 70, as well as the keys of group 72, and even the alpha-numeric keys in appropriate sequence can be used to initiate functions such as timer set, setting of number of beats, setting of gain, setting of time base, setting of patient or user codes, calibration, inserting of artifact filter, reset, selection of functions or the like. Each key can perform more than one function depending on the setting of other keys. The device may function, either by selection or program in several modes. First, the device can automatically and sequentially produce a pre-selected series of single graphical printouts, each representative of a separate phono- or electrocardiograph output. Second, selected ones of the outputs can be printed. Third, up to four selected outputs such as a phono- and three electrocardiograph output can be printed simultaneously, side by side. By selection of the printer, even more of the outputs can be printed side by side, provided adequate memory capacity is provided.

Information can be printed before or after each curve or even next to each curve. In addition to curve identification, date, time and patient identification information, the degree of filtering, the time base, the gain (sensitivity) or other relevant information can be printed to provide the user with a full record of what is shown on the cardiogram.

It should also be understood that in an alternative embodiment of a phono- and electrocardiograph in accordance with the invention, printing does not commence until all input data signals have been stored in memory. Also each memory address may store data of more than one input jacks 14, 20.

EPROM 60 may have stored therein programs permitting analysis of ECG and PCG data under the control of microprocessor 52. Specifically, spectral analysis of the data can be performed, or the data can be subjected to fast fourier transforms, the results of which can be used in diagnosis. These results can be stored in RAM 50, printed by printer 26, displayed on display 24 or even stored in micro-cassette 66. The results can be in the form of numerical values or graphical presentations. An example of a graphical presentation resulting from analysis of input data is the presentation of a histogram which presents a graphical presentation of heart rate over time. Another example of analysis would be the performance of actual diagnostics or the detection of abnormalities through examination of the data passing through RAM 50 by means of a program stored in EPROM 60.

Still another feature of the invention is the storage in EPROM 60 of data representative of the typical waveforms for various abnormal conditions. The user can elect to have the waveforms displayed on display 24 or printed by printer 26 by providing commands through keyboard 22 to microprocessor 52. The display can position the typical abnormal waveform and the actual patient ECG waveform in side-by-side relation and in synchronization. Thus, by way of example, while normally waveforms 84a, 84b and 84c (FIG. 1) might be patient ECG waveforms and waveform 84d might be patient PCG data, one of the waveforms can be replaced by the typical abnormality waveform selected by the user.

As mentioned above, the signal from an auxiliary device may be applied at jack 20, for the purpose of displaying a waveform representative of that signal on display 24, for the purpose of printing the waveform version of the signal by printer 26 or for the purpose of storing the signal in RAM 50 or micro-cassette 66. By use of keyboard 22, the user can instruct the microprocessor as to the nature of the input (whether it is the output of an electronic stethoscope or of another auxiliary device, and can further instruct the microprocessor as to how to deal with the data. One example of an auxiliary device is a differential doppler for blood flow measurement as disclosed in my pending U.S. patent application Ser. No. 592,490, filed Mar. 23, 1984. This device is adapted to determine the degree of occlusion in a blood vessel. The apparatus includes a transmitter for producing an ultrasonic signal, first probe for directing the ultrasonic signal to a first location in a blood vessel and a second probe for directing an ultrsonic signal to a second location in a blood vessel. A first receiver receives the ultrasonic signal after return from contact with blood flowing in the blood vessel at the first location and produces a first received signal repretative thereof. A second receiver receives the ultrasonic signal after returning from contact with the blood vessel at the second location and produces a second receive signal representative thereof. A different measuring circuit receives the first and second received signals and produces a difference signal representative of the difference between the first and second received signals and a difference in blood flow velocity at the first and second locations can be determined. This difference signal can be applied to the PCG/AUX input jack 20 of phono- and electrocardiograph 10 or to a separate jack 21 shown in phantom in FIG. 4, if desired. The resulting signal can be analyzed by programs stored in the EPROM 60 and the data can be considered in conjunction with the ECG or PCG data for the purpose of analysis, including the determination of blood pressure and arterial pulse rate.

In one embodiment capable of printing two side-by-side waveforms, the case is about 4.0 inches wide, 6.75 inches long and 1.5 inches thick. In a second embodiment is shown in FIG. 1, the case is about 6.0 inches wide but otherwise of about the same length and thickness. The phono- and electrocardiograph thus formed in readily portable and easily used.

It will thus be seen that the objects set forth above, among those made apparent from the preceding description, are efficiently attained and, since certain changes may be made in the above construction without departing from the spirit and scope of the invention, it is intended that all matter contained in the above description as shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An electrocardiograph for connection to sensors outputting analog electrical signals, comprising:
   at least one sensor outputting analog electrical signals;
   sampling means for selectively sensing at intervals at least one analog signal representative of the analog signals from at least one of said sensors;
   analog to digital conversion means for receiving said sampled analog signals and outputting digitized signals corresponding thereto;
   memory means including a plurality of addresses for storage of data therein;
   processor means for writing said consecutively sampled digitized signals representative of a predetermined duration of the at least one analog sensor output signal into said addresses of said memory means for storage therein in consecutive order;
   printer means for recording on a print medium in response to digital data input thereto, said processor means including reading means for reading said stored data from said addresses in said memory means in said consecutive order and input said data to said printer means for printing a series of portions of a curve representative of the analog signal from said at least one sensor, said printer means including medium advance means for moving said print medium after printing each said curve portion, a cardiogram of said predetermined duration of said selectively sensed at least one analog signal being produced on said print medium extending in the direction of advance of said print medium; and
   case means for carrying said sampling means, analog to digital conversion means, memory means, processor means and printer means, said case means and contents being dimensioned and of a weight to be conveniently hand held for ease or portability.

2. An electrocardiograph as claimed in claim 1, including magnetic tape cassette means carried by said case means for storing consecutively sampled digitized signals under the control of said processor means.

3. An electrocardiograph as claimed in claim 2, and including keyboard means coupled to said processor means for the selective control of the application of said consecutively sampled digitized signals to said cassette means.

4. An electrocardiograph as claimed in claim 3, wherein said processor means is coupled to control the application of consecutively sampled digitized signals from said cassette means to said printer means.

5. An electrocardiograph as claimed in claim 4, including matrix display means capable of displaying curves representative of the analog signal from said at least one sensor, said processor means further including a sampling means for applying, at the direction of said keyboard means, said consecutively sampled digitized signals from either said memory means or said cassette means to said display means for display thereby.

6. An electrocardiograph as recited in claim 1, and including dot matrix display means, said processor means further including a selection means for selectively applying said consecutively sampled digitized signals of said display means for the display of a curve representative of the analog signal from said at least one sensor on said display means.

7. An electrocardiograph as recited in claim 1, and including instrument amplifier means for receiving the analog electrical signal from at least one sensor and amplifying same;
   means for selectively adjusting the gain of said amplification; and
   means for filtering said analog electrical signal to remove undesired elements.

8. An electrocardiograph as claimed in claim 7, and including a plurality of sensors outputting analog electrical signals;
   lead select circuit means for receiving said plurality of analog electrical signals and for producing at least two selected, desired analog electrical signals;
   an instrument amplifier means, gain adjustment means and filter means for receiving each of said analog electrical signals from said lead select circuit, said sampling means including multiplex means for sampling each of said at least two analog electrical signals for application to said analog to digital conversion means.

9. An electrocardiograph as recited in claim 8, wherein said filter means includes a first filter means for filtering the analog electrical signal applied thereto to a first frequency range and a second filter means for filtering signals from said first filter means to a still narrower frequency range, said processor means being coupled to selectively apply the output of the first or second filter means to said sampling means.

10. The electrocardiograph as recited in claim 9, wherein said second filter means is an artifact filter means.

11. An electrocardiograph as recited in claim 1, and including speaker means, said processor means further including an energizing means for energizing said speaker means in response to predetermined states of said sample digitized signals.

12. An electrocardiograph as recited in claim 11, wherein the predetermined state of said sample digitized signals is the cessation of the natural R-wave.

13. An electrocardiograph as recited in claim 12, wherein the predetermined state of said sample digitized signal is additionally a heart rate above or below selected values, said processor means further including an actuation means for actuating said speaker means to produce a different audible sound when detecting cessation of natural R-waves than when detecting heart rate above or below selected values.

14. The electrocardiograph as recited in claim 11, including voice synthesizer means under the control of the processor means for providing verbal instructions for use and alarm information to the user.

15. An electrocardiograph as recited in claim 1, and including data representative of curves of typical normal ECGs, said processor means further including a selection means for selectively applying said stored typical ECG curves to said printer means for recording on a print medium.

16. An electrocardiograph as recited in claim 15, wherein said printer means further includes a graphing means for simultaneously producing two side-by-side curves extending in the direction of the advance of said print medium, said processor means further including a control means for printing the curve representative of typical ECGs and the curve representative of the analog signal from said at least one sensor in side-by-side relation.

17. An electrocardiograph as recited in claim 16, wherein said processor means further includes a second control means for printing said side-by-side curves in essential synchronization.

18. An electrocardiograph as recited in claim 1, wherein said memory means stores a program for analysis of the sampled digitized signals under the control of said processor means, said processor means further including driving means for applying the data representative of the results of such analysis to said printer means for recording on a print medium.

19. An electrocardiograph as recited in claim 18, and including display means, said processor means further including a further driving means for applying the data representative of the results of said analysis to said display means for display thereon.

20. An electrocardiograph as recited in claim 18, wherein said program produces a histograph representative of heart rate over time.

21. An electrocardiograph as recited in claim 18, wherein said stored program applies fast fourier transforms to said sample digitized signals.

22. An electrocardiograph as recited in claim 18, and including an auxiliary input means receiving an auxiliary analog signal, the program stored in said memory means analyzing said auxiliary signal.

23. The electrocardiograph as recited in claim 21, and said auxiliary signals the output of a differential doppler for blood flow measurement.

24. An electrocardiograph as claimed in claim 1, including means for combining the outputs of at least two of said sensors so that at least one of said at least one sampled analog signals represents a combination of the outputs of at least two of said sensors.

25. An electrocardiograph as claimed in claim 1, including multiplexing means coupled intermediate said sensor outputs and said sampling means so that said processor means writes said digitized signals into and reads out said stored signals from said memory means for printing on a multiplexed basis.

26. An electrocardiograph as claimed in claim 1, wherein said sensors include at least one phono-cardiograph sensing element and a plurality of electrocardiograph sensing elements.

27. An electrocardiograph as recited in claims 1, 24 or 26, wherein the quantity of said analog signals is at lest two, each such analog signal being from at least one of said sensors and said sampling means includes multiplexing means, said analog sensor signals being input to said analog to digital conversion means on a multiplexed basis, the reading means of said processor means inputting data to said printer means to successively print essentially side-by-side portions of at least two side-by-side cardiograms on said print medium, and to print a series of such side-by-side portions of cardiograms curves on the print medium, said medium advancing means moving the print medium after side-by-side printing at each side-by-side pair of curved portions, both cardiograms extending in the direction of advance of said print medium.

28. An electrocardiograph as claimed in claim 27, wherein said multiplexing means is controlled by said processor means.

29. An electrocardiograph as claimed in claim 28, and further comprising external selection means for selecting analog signals for data storage and print out from among the available analog signals.

30. An electrocardiograph as claimed in claim 29, wherein said selection means includes a keyboard operable by the user of said electrocardiograph, said analog signals being selected for print-out by keyboard inputs.

31. An electrocardiograph as recited in claim 29, and further comprising visual display means, said display means including means for visibly indicating which of said sensor signals have been selected for data storage and print out by operation of said selection means.

32. An electrocardiograph as claimed in claim 31, wherein said memory means further includes instructions stored in digital format in a portion of said addresses, said processor means including decoder means for decoding said instructions, and visibly displaying said display means including alphanumerical means for said instructions directing the user in correct operating procedures for said electrocardiograph.

33. An electrocardiograph as claimed in claim 31, wherein said displayed correct procedures specify at least in part operation of said external selection means by said user.

34. An electrocardiograph as claimed in claim 33, wherein said selection means included a keyboard operated by the use of the electrocardiograph, said display means including means for visibly verifying the inputs to the keyboard by the user.

35. An electrocardiograph as claimed in claim 27, wherein said printer means includes a print head mounted on a carriage for translation laterally across said print medium, and printer interface means coupled to said processor means for driving said head for printing on said medium wherever the lateral position of said carriage corresponds to said digitized data stored in and read from said memory means, said processor means directing read-out digitized data to said printer interface means.

36. An electrocardiograph as recited in claim 35, wherein said printer includes a paper feed means and a displacement means for the coordinate displacement of said paper feed means and said print head to effect printing.

37. An electrocardiograph as recited in claim 1 and further comprising signal conditioning means coupled intermediate said at least one sensor and said sampling means for receiving said analog sensor signals and adjusting said signals for full scale print out on said print medium, said signal conditioning means further including a mixing means for mixing said analog signals from a plurality of said sensors.

38. An electrocardiograph as recited in claim 37, wherein said mixing means combines at least two of said analog sensor signals to output average and difference signals of said sensor signals to said sampling means.

39. An electrocardiograph as recited in claim 1, wherein operating instructions for said processor means are stored in a portion of said addresses.

40. An electrocardiograph as claimed in claim 1, and further comprising an output terminal on said cardiograph and means for selectively coupling at least one analog output signal from said sensors to one said output terminal.

41. An electrocardiograph as recited in claim 1, and further comprising an output terminal on said cardiograph, and said processor means further including an output means for reading digitized data from said memory means and applying said data to said output terminal.

* * * * *